(12) United States Patent
Vos et al.

(10) Patent No.: US 11,346,334 B2
(45) Date of Patent: May 31, 2022

(54) METHOD FOR REPEATABLE AND ACCURATE DISPENSING OF FLUIDS CONTAINING SOLIDS

(71) Applicant: Halliburton Energy Services, Inc., Houston, TX (US)

(72) Inventors: Andrew D. Vos, Spring, TX (US); Dale E. Jamison, Humble, TX (US); Adam R. Dotson, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 400 days.

(21) Appl. No.: 16/612,524

(22) PCT Filed: Dec. 20, 2018

(86) PCT No.: PCT/US2018/066911
§ 371 (c)(1),
(2) Date: Nov. 11, 2019

(87) PCT Pub. No.: WO2020/131083
PCT Pub. Date: Jun. 25, 2020

(65) Prior Publication Data
US 2021/0048014 A1     Feb. 18, 2021

(51) Int. Cl.
*F04B 45/053* (2006.01)
*E21B 21/01* (2006.01)
*G01N 33/28* (2006.01)

(52) U.S. Cl.
CPC .......... *F04B 45/0533* (2013.01); *E21B 21/01* (2013.01); *G01N 33/2823* (2013.01)

(58) Field of Classification Search
CPC ...... F04B 45/0533; E21B 21/01; E21B 21/06; G01N 33/2823

(Continued)

(56) References Cited

U.S. PATENT DOCUMENTS 3,321,977 A * 5/1967 Topham ................. G01N 30/20
                                                  417/401
4,316,482 A   2/1982 Pearce et al.
(Continued)

FOREIGN PATENT DOCUMENTS

WO    WO-2015096885 A1 *  7/2015  ............... A61L 2/28

OTHER PUBLICATIONS

ISRWO International Search Report and Written Opinion for PCT/US2018/066911 dated Sep. 11, 2019.

*Primary Examiner* — Nimeshkumar D Patel
*Assistant Examiner* — Jean F Morello
(74) *Attorney, Agent, or Firm* — Tenley Krueger; C. Tumey Law Group PLLC

(57) ABSTRACT

A system or method for monitoring drilling fluid. The system may comprise a fluid supply, wherein the fluid supply houses a drilling fluid, a pump, wherein the pump is fluidly connected to the fluid supply, a dispensation unit, wherein the dispensation unit is fluidly connected to the pump, and a process vessel, wherein the process vessel is fluidly coupled to the dispensation unit. The dispensation unit may comprise a housing, wherein the housing may comprise an internal cavity, an inlet, and an outlet. The dispensation unit may further comprise a top plate, wherein the top plate is configured to form a seal over the housing, and a diaphragm, wherein the diaphragm is disposed between the top plate and the housing. A method may comprise pumping the drilling fluid through a dispensation unit, actuating the dispensation unit, and determining a property of the drilling fluid.

20 Claims, 8 Drawing Sheets

(58) Field of Classification Search
USPC .................................................. 73/152.19
See application file for complete search history.

(56) References Cited

U.S. PATENT DOCUMENTS

| | | |
|---|---|---|
| 4,505,451 A | 3/1985 | Jonas |
| 5,215,216 A | 6/1993 | Van Marcke |
| 5,823,509 A | 10/1998 | Daniels |
| 6,065,940 A | 5/2000 | Fleischer et al. |
| 2005/0184087 A1 | 8/2005 | Zagars et al. |
| 2018/0003654 A1 | 1/2018 | Chen et al. |
| 2018/0100392 A1 | 4/2018 | Kleinguetl et al. |
| 2018/0203029 A1 | 7/2018 | Hamasaki et al. |

\* cited by examiner

METHOD FOR REPEATABLE AND ACCURATE DISPENSING OF FLUIDS CONTAINING SOLIDS

BACKGROUND

During the drilling of a wellbore into a subterranean formation, a drilling fluid, also referred to as a drilling mud, may be continuously circulated from the well surface down to the bottom of the wellbore being drilled and back to the well surface again. The drilling fluid may include a mixture of water, oil, additives (e.g., viscosifiers, weighting materials, emulsifying surfactants, and the like), and combinations thereof, to impart certain properties to the drilling fluid to satisfy drilling requirements.

Drilling fluid may serve several functions, one of them being to transport wellbore cuttings up to the surface where they are separated from the drilling fluid. Another function of the drilling fluid may include providing hydrostatic pressure against the wall of the drilled wellbore, thereby preventing wellbore collapse and the resulting influx of gas or liquid from a formation being penetrated. The density of drilling fluid may be maintained, for example, to control the hydrostatic pressure that drilling exerts at the bottom of the wellbore. It may be desired to monitor properties of drilling fluid, for example, to determine whether drilling fluid satisfies various drilling requirements. Such properties may include, but are not limited to, density, viscosity, gel strength, and solids content, among others. Accurate determination of fluid properties may be problematic using current technologies as precise dispensation of fluid samples of drilling fluid traditionally may include sliding or rotating sealing components that may be prone to wear and leakage when interacting with fluids containing solid particulates. Over time, these components may break down and cause equipment failure. It may be beneficial to accurately sample drilling fluid using a system that does not rely on moving sealing components.

BRIEF DESCRIPTION OF THE DRAWINGS

These drawings illustrate certain aspects of some of the embodiments of the present disclosure, and should not be used to limit or define the disclosure.

DETAILED DESCRIPTION

This disclosure may generally relate to operations concerning analyzing a fluid sample. More particularly, systems and methods may be provided for determining the properties of a fluid sample taken from a drilling fluid in a circulating in a fluid circuit. These systems and methods may use a dispensation unit to remove a pre-determined volume of fluid from the circulation of a drilling fluid containing solid particulates.

Figure 1:
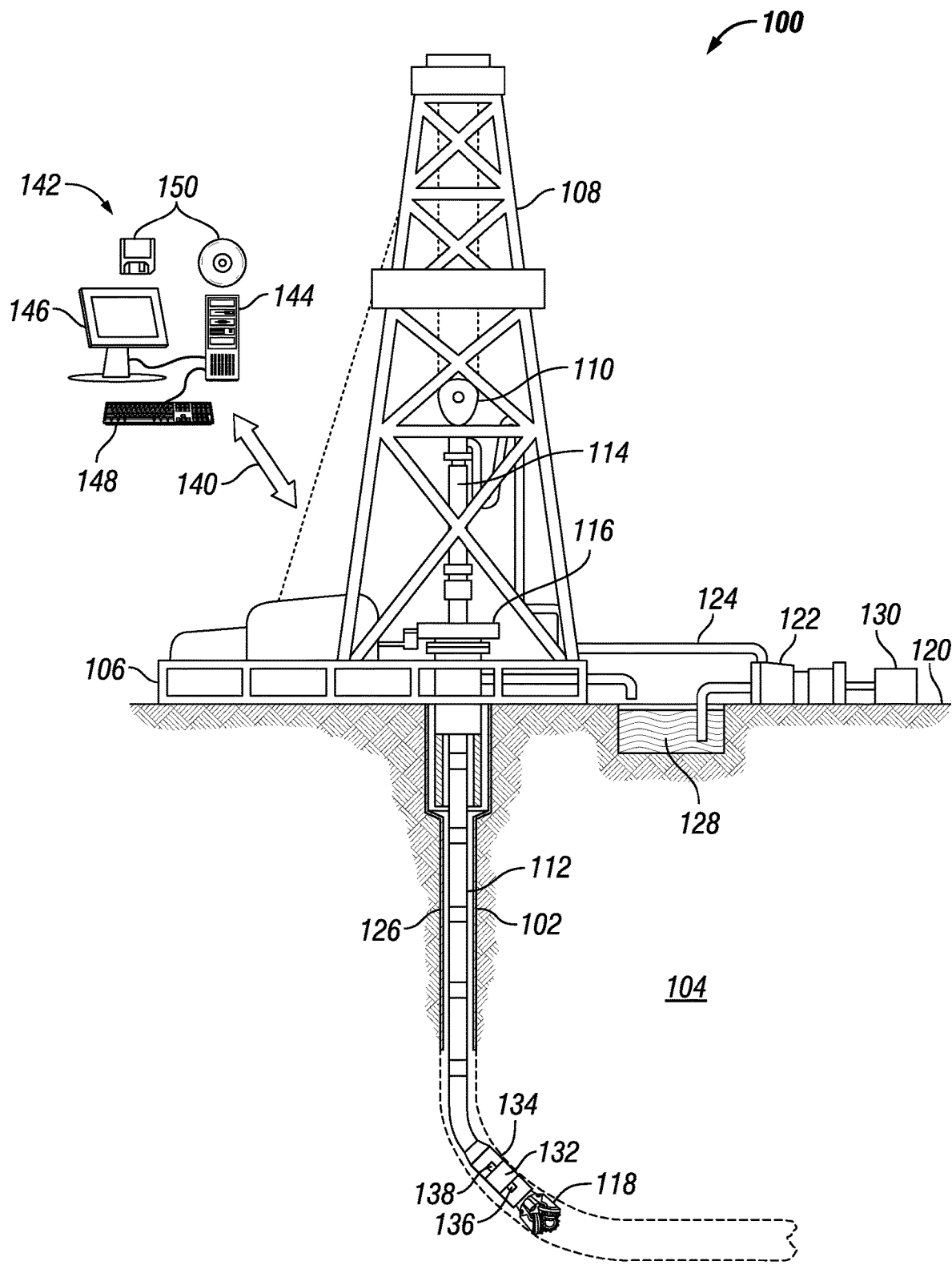
FIG. 1 illustrates an example of a well system.

FIG. 1 illustrates a well system 100. As illustrated, a wellbore 102 may extend through a subterranean formation 104. While the wellbore 102 is shown extending generally vertically into the subterranean formation 104, the principles described herein are also applicable to wellbores that extend at an angle through the subterranean formation 104, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a drilling platform 106 may support a derrick 108 having a traveling block 110 for raising and lowering a drill string 112. Drill string 112 may include, but is not limited to, drill pipe and coiled tubing, as generally known to those skilled in the art. A kelly 114 may support drill string 112 as it may be lowered through a rotary table 116. A drill bit 118 may be attached to the distal end of drill string 112 and may be driven either by a downhole motor and/or via rotation of drill string 112 from a surface 120. Without limitation, drill bit 118 may include, roller cone bits, PDC bits, natural diamond bits, any hole openers, reamers, coring bits, and the like. As drill bit 118 rotates, it may create and extend wellbore 102 to penetrate various subterranean formations 104. A pump 122 may circulate a particulate-containing fluid, such as drilling fluid, through a feed pipe 124 to kelly 114, downhole through interior of drill string 112, through orifices in drill bit 118, back to surface 120 via annulus 126 surrounding drill string 112, and into a fluid supply 128. Without limitations, fluid supply 128 may be a mud pit that serves as a containment unit for the particulate-containing fluid. A dispensation unit 130 may be disposed at surface 120 and incorporated in-line with the circulation of the particulate-containing fluid. Without limitations, the particulates present within the particulate-containing fluid may be solids such as sand, drill cuttings, clays, and/or the like.

Drill bit 118 may be just one piece of a downhole assembly that may include one or more drill collars 132. One or more of the drill collars 132 may form a tool body 134, which may be elongated as shown on FIG. 1. Tool body 134 may be any suitable material, including without limitation titanium, stainless steel, alloys, plastic, combinations thereof, and the like. Drill bit 118 may further include one or more sensors 136 for measuring properties of the reservoir fluid, wellbore 102, subterranean formation 104, and/or the like.

Drill bit 118 may further include a communication module 138. Communication module 138 may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, communication module 138 may include random access memory (RAM), one or more processing units, such as a central processing unit (CPU), or hardware or software control logic, ROM, and/or other types of nonvolatile memory.

Any suitable technique may be used for transmitting signals from communication module 138 to the surface 120. As illustrated, a communication link 140 (which may be wired or wireless, for example) may be provided that may transmit data from communication module 138 to an information handling system 142 at surface 120. Information handling system 142 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, an information handling system 142 may be a personal computer, a network storage device, or any other suitable device and may vary in size, shape, performance, functionality, and price. Information handling system 142 may include random access memory (RAM), one or more processing resources such as a central processing unit (CPU) 144 or hardware or software control logic, ROM, and/or other types of nonvolatile memory. Additional components of the information handling system 142 may include one or more disk drives, output devices, such as a video display 146, and one or more network ports for communication with external devices as well as an input device 148 (e.g., keyboard, mouse, etc.). Information handling system 142 may also include one or more buses operable to transmit communications between the various hardware components.

Alternatively, systems and methods of the present disclosure may be implemented, at least in part, with non-transitory computer-readable media 150. Non-transitory computer-readable media 150 may include any instrumentality or aggregation of instrumentalities that may retain data and/or instructions for a period of time. Non-transitory computer-readable media 150 may include, for example, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

In examples, the information handling system 142 may act as a control system and possibly a data processing system that analyzes information collected using dispensation unit 130. Dispensation unit 130 may operate to collect a predetermined volume of fluid used during operations at well system 100. Dispensation unit 130 may be disposed at surface 120 and may be in fluid communication with pump 122, fluid supply 128, and/or combinations thereof. In examples, dispensation unit 130 may be directly connected to fluid supply 128 and may serve to analyze a sample of the fluid contained within fluid supply 128. Dispensation unit 130 may be integrated into a configuration providing a parallel flow path for a potential fluid used in drilling operations. During operations, the fluid may circulate throughout well system 100 with or without flowing through dispensation unit 130. In certain examples, a suitable fluid restrictor may be disposed upstream of dispensation unit 130 to reduce the fluid pressure of a fluid prior to entering dispensation unit 130. Without limitations, the fluid restrictor may be a nozzle, a vortex, a change in tubing and/or pipe diameter, fluid diode, and/or other centrifugal fluid selector.

In other examples, dispensation unit 130 may be disposed within a separate piece of equipment at the well site and may operate in tandem with said piece of equipment. As dispensation unit 130 is disposed in-line with a potential flow path of the appropriate fluid, dispensation unit 130 may operate without interrupting other operations (i.e., drilling or completion operations).

Figure 2:
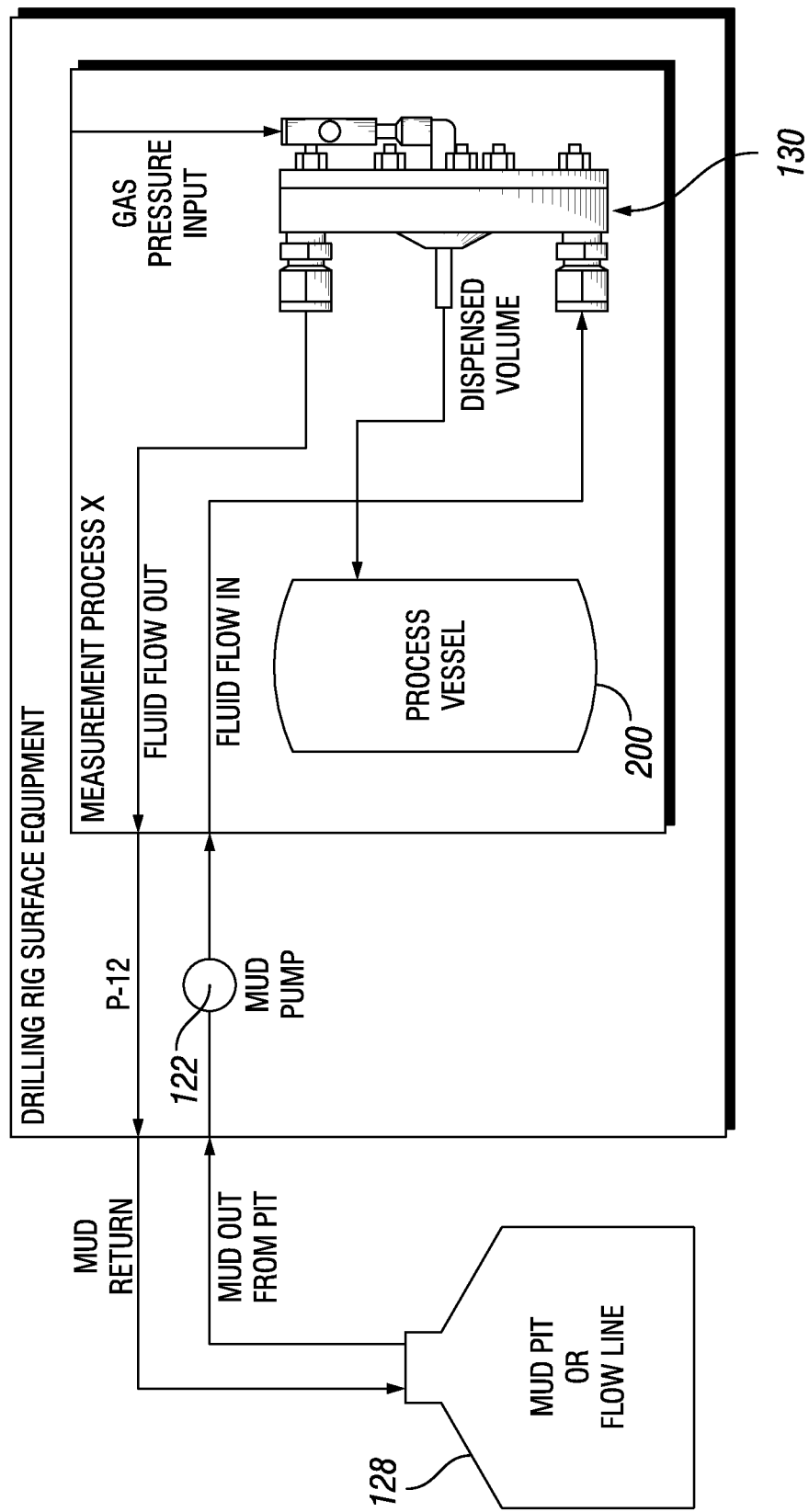
FIG. 2 illustrates a schematic diagram of the arrangement of a pump, a fluid supply, and a dispensation unit.

FIG. 2 illustrates a schematic diagram of the arrangement of pump 122, fluid supply 128, and dispensation unit 130 wherein each piece of equipment may be utilized to collectively sample a drilling fluid. Pump 122, fluid supply 128, and dispensation unit 130 may be connected to each other through the use of any suitable piping. As illustrated, pump 122 may operate to pull the particulate-containing fluid from fluid supply 128, displace the particulate-containing fluid into and through dispensation unit 130, and return the particulate-containing fluid back to fluid supply 128. In examples, pump 122, fluid supply 128, and dispensation unit 130 may operate in a feedback loop. As illustrated, there may be a process vessel 200 coupled to dispensation unit 130. Process vessel 200 may be coupled to dispensation unit 130 by using any suitable mechanism including, but not limited to, the use of suitable fasteners, threading, adhesives, welding and/or any combination thereof. Without limitation, suitable fasteners may include nuts and bolts, washers, screws, pins, sockets, rods and studs, hinges and/or any combination thereof. Process vessel 200 may be any suitable size, height, and/or shape to receive a specified volume of particulate-containing fluid from dispensation unit 130. Without limitation, a suitable shape may include, but is not limited to, cross-sectional shapes that are circular, elliptical, triangular, rectangular, square, hexagonal, and/or combinations thereof. In examples, process vessel 200 may derive a property of the particulate-containing fluid. Without limitations, any suitable property such as density, salinity, electrical conductivity, thermal conductivity, compressibility, viscosity, rheology, oil to water ratio, capacitance, electrical impedance, emulsion stability (ES, API test method) and/or combinations thereof may be determined. Process vessel 200 may include at least one sensor (not illustrated) to measure the sample of the particulate-containing fluid. Without limitations, the at least one sensor may be an electrical impedance sensor for use in spectroscopy or as an integrated computational element (ICE), an optical sensor, viscometer, rheometer, electrostatic separator. In examples, the at least one sensor may measure microwaves, vibration attenuation, zeta potential, fluorescence, dielectric constant, electrophoretic separation, and/or combinations thereof. As the particulate-containing fluid flows through the feedback loop of pump 122, fluid supply 128, and dispensation unit 130, process vessel 200 may not receive a sample until dispensation unit 130 is actuated. There may be various embodiments of dispensation unit 130 and methods of actuating dispensation unit 130 in order to dispense a volume of particulate-containing fluid to be sampled.

Figure 3:
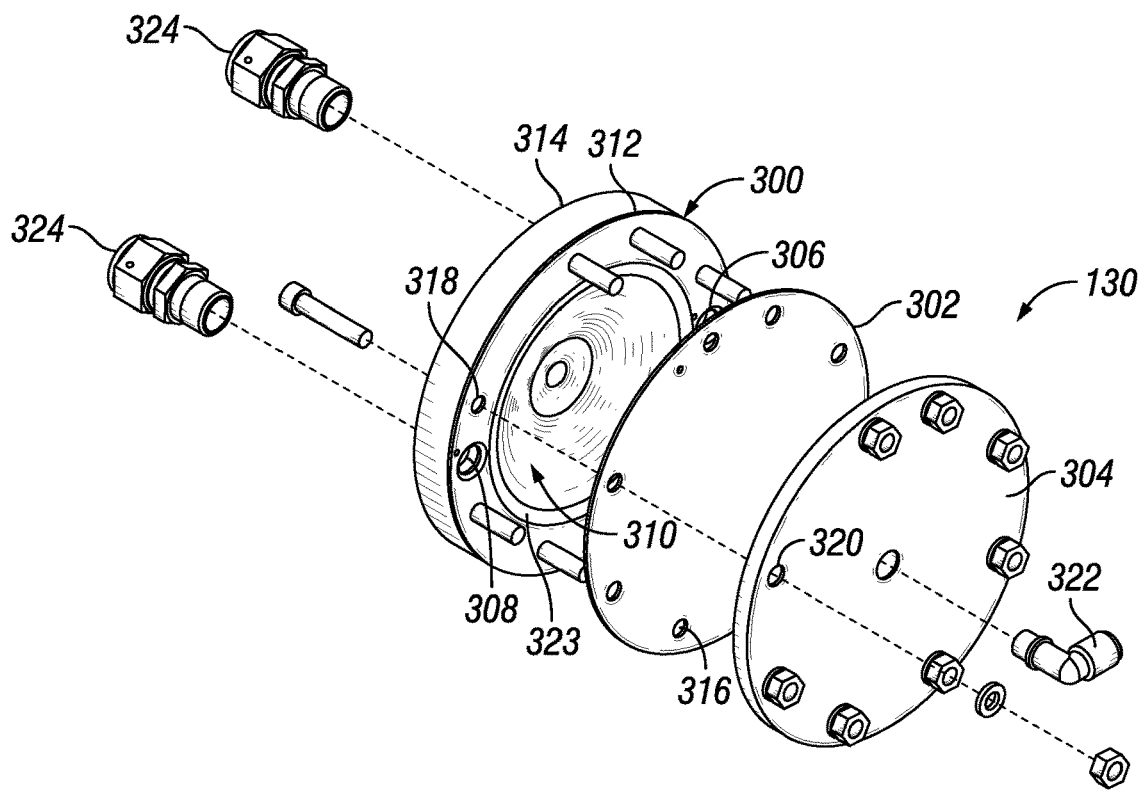
FIG. 3 illustrates an exploded, isometric view of the components of a dispensation unit.
Figure 4:
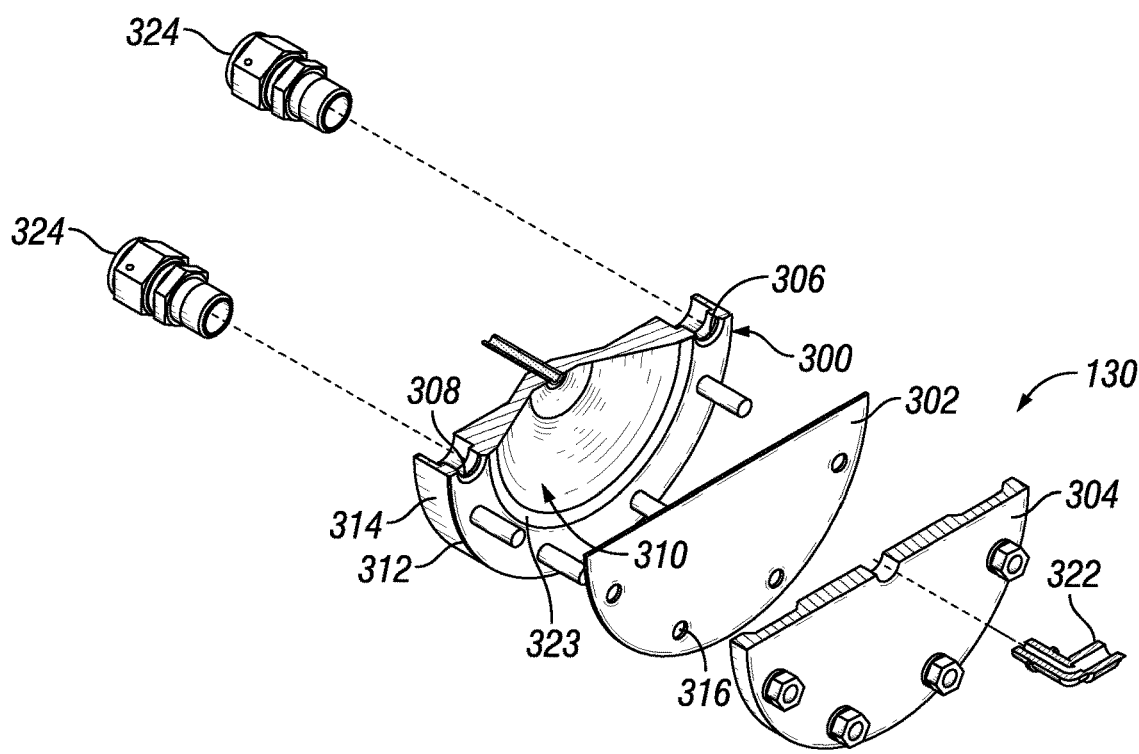
FIG. 4 illustrates an exploded, cross-sectional, isometric view of the components of a dispensation unit.
Figure 5:
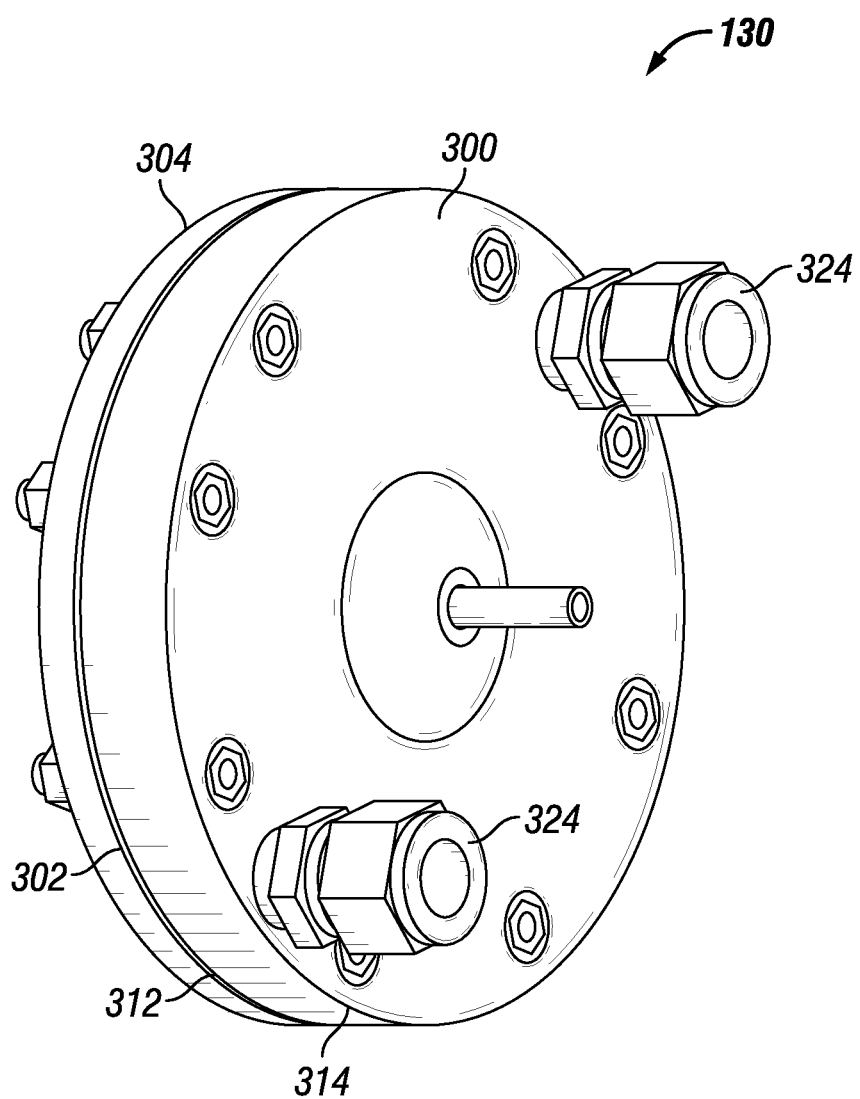
FIG. 5 illustrates a bottom, isometric view of a dispensation unit.

FIGS. 3-5 illustrate different views of dispensation unit 130. FIG. 3 illustrates an exploded, isometric view of the components of dispensation unit 130. FIG. 4 illustrates an exploded, cross-sectional, isometric view of the components of dispensation unit 130. FIG. 5 illustrates a bottom, isometric view of dispensation unit 130. Dispensation unit 130 may serve to remove a pre-defined volumetric amount of fluid from the feedback loop circulating the particulate-containing fluid to be tested by process vessel 200 (i.e., referring to FIG. 2). Without limitations, dispensation unit 130 may include a housing 300, a diaphragm 302, a top plate 304, an inlet 306, and an outlet 308.

Housing 300 may form the structure of dispensation unit 130 that contains the particulate-containing fluid as the particulate-containing fluid flows into and out of dispensation unit 130. Housing 300 may be any suitable size, height, and/or shape. Without limitation, a suitable shape may include, but is not limited to, cross-sectional shapes that are circular, elliptical, triangular, rectangular, square, hexagonal, and/or combinations thereof. In examples, housing 300 may have a circular cross-sectional shape. Housing 300 may be made from any suitable material. Suitable materials may include, but are not limited to, metals, nonmetals, polymers, ceramics, and/or combinations thereof. Housing 300 may include an internal cavity 310. Internal cavity 310 may be an absence of material designated as the space in which to be filled by the particulate-containing fluid. Internal cavity 310 may be concentric with the central axis of housing 300. Internal cavity 310 may be any suitable size, height, and/or shape. The height of internal cavity 310 may be defined as the thickness of housing 300, which may be the distance from a first end 312 of housing 300 to a second end 314 of housing 300. Without limitation, the volume of internal cavity 310 may be about 10 milliliters to about 50 milliliters, about 30 milliliters to about 60 milliliters, about 40 milliliters to about 80 milliliters, or about 50 milliliters to about 100 milliliters. Without limitation, a suitable shape may include, but is not limited to, cross-sectional shapes that are circular, elliptical, triangular, rectangular, square, hexagonal, and/or combinations thereof. In examples, internal cavity 310 may have a circular cross-sectional shape that decreases as the height of internal cavity 310 increases. Internal cavity 310 may be sealed with diaphragm 302.

Diaphragm 302 may be any suitable size, height, and/or shape. Without limitation, a suitable shape may include, but is not limited to, cross-sectional shapes that are circular, elliptical, triangular, rectangular, square, hexagonal, and/or combinations thereof. In examples, diaphragm 302 may have a circular cross-sectional shape that has a diameter equivalent to the outer diameter of housing 300. Diaphragm 302 may be made from any suitable material that may be flexible. Without limitations, diaphragm 302 may be an elastomer. In examples, diaphragm 302 may be actuated to flex into internal cavity 310 (as discussed further below). Diaphragm 302 may be used to force out any particulate-containing fluid from within internal cavity 310. Depending on the force used for actuation, diaphragm 302 may be displaced to line the walls of internal cavity 310. In examples, diaphragm 302 may be disposed on top of housing 300. There may be a first set of holes 316 present in diaphragm 302 that align with a second set of holes 318 disposed in housing 300. In examples, any suitable fastener may be used to fasten housing 300 and diaphragm 302 to top plate 304. Without limitation, suitable fasteners may include nuts and bolts, washers, screws, pins, sockets, rods and studs, hinges and/or any combination thereof.

Top plate 304 may be a protective piece of material that seals diaphragm 302 to housing 300. In examples, top plate 304 includes an inner surface and an outer surface. Then inner surface of top plate 304 is defined as the surface area of top plate 304 which faces internal cavity 310 and the outer surface of top plate 304 is the surface area of top plate 304 with faces away from internal cavity 310. There may be a third set of holes 320 disposed on top plate 304 that align with both first set of holes 316 and second set of holes 318. As depicted, suitable fasteners may be used to secure diaphragm 302 between top plate 304 and housing 300. Top plate 304 may be any suitable size, height, and/or shape. Without limitation, a suitable shape may include, but is not limited to, cross-sectional shapes that are circular, elliptical, triangular, rectangular, square, hexagonal, and/or combinations thereof. In examples, top plate 304 may have a circular cross-sectional shape that has a diameter equivalent to the outer diameter of housing 300. Top plate 304 may further include a coupling 322. Coupling 322 may be any suitable coupling to connect an external source of compressed gas (not illustrated) to dispensation unit 130. Without limitations, the external source of compressed gas may be supplied through any suitable line attached to dispensation unit 130 through coupling 322. Pressurizing dispensation unit 130 with the use of external source of compressed gas connected to coupling 322 may push diaphragm 302 to cover inlet 306 and outlet 308, thus creating a pressure-tight seal. In examples, coupling 322 may be disposed at any suitable location on top plate 304. Coupling 322 may be disposed on to top plate 304 by using any suitable mechanism including, but not limited to, the use of suitable fasteners, threading, adhesives, welding and/or any combination thereof.

In examples, particulate-containing fluid may flow into dispensation unit 130 through inlet 306 and out of dispensation unit 130 through outlet 308. Inlet 306 and outlet 308 may be openings within housing 300 to allow fluid communication between dispensation unit 130 and fluid supply 128 (i.e., referring to FIG. 1). Inlet 306 and outlet 308 may be any suitable size and shape. As depicted in FIGS. 3-5, inlet 306 may be disposed opposite from outlet 308. Both inlet 306 and outlet 308 may be disposed between a chamfer 323 defining the transition between housing 300 and internal cavity 310 and the outer diameter of housing 300. In examples, a set of couplings 324 may be disposed within inlet 306 and outlet 308. The set of couplings 324 may be attached to ends of external piping leading to and/or from fluid supply 128.

Figure 6:
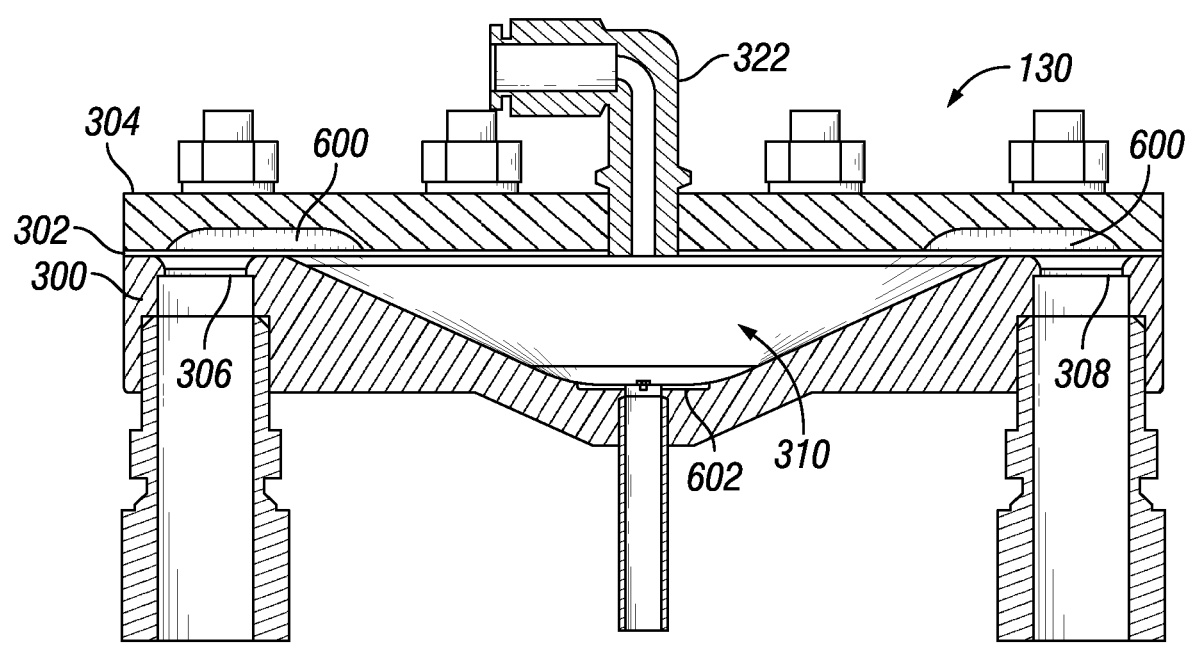
FIG. 6 illustrates a stage of operation of a dispensation unit.

FIG. 6 illustrates a stages of operation with dispensation unit 130. In examples, particulate-containing fluid may be pumped into dispensation unit 130 through inlet 306. As diaphragm 302 may be disposed between top plate 304 and housing 300, diaphragm 302 may block the flow of the particulate-containing fluid into and/or out of dispensation unit 130. As the particulate-containing fluid travels through inlet 306, the pressure of the fluid may cause diaphragm 302 to displace into a recess 600 within top plate 304. Recess 600 may be any suitable size, height, and/or shape. Without limitation, a suitable shape may include, but is not limited to, cross-sectional shapes that are circular, elliptical, triangular, rectangular, square, hexagonal, and/or combinations thereof. There may be a plurality of recesses 600 disposed within top plate 304. In examples, the number of recesses 600 may be equivalent to the number of inlets 306 and outlets 308 and may be disposed above inlet 306 and outlet 308 within top plate 304. As diaphragm 302 displaces into recess 600, the particulate-containing fluid may flow into internal cavity 310. The volume of internal cavity 310 may be filled with the particulate-containing fluid. As the particulate-containing fluid begins to exceed the volume of internal cavity 310, the pressure of the particulate-containing fluid may force diaphragm 302 to displace into recess 600 disposed above outlet 308. Once the entrance into outlet 308 is unobstructed by diaphragm 302, the particulate-containing fluid may flow through outlet 308 and out of dispensation unit 130.

In order to displace the particulate-containing fluid from internal cavity 310 towards process vessel 200 (i.e., referring to FIG. 2), diaphragm 302 may be actuated to displace downwards into internal cavity 310. In examples, an external gas source (not illustrated) may be coupled to top plate 304 through the use of coupling 322. The external gas source may supply pressure onto diaphragm 302. As the pressure increases, diaphragm 302 may displace downwards to seal off inlet 306 and/or outlet 308 to maintain a fixed volume within internal cavity 310. There may be a valve 602 disposed in housing 300 to release the fixed volume of particulate-containing fluid from internal cavity 310. Without limitations, valve 602 may be any suitable valve including, but not limited to, a ball valve, diaphragm valve, check valve, gate valve, bladder valve, pinch valve, and/or butterfly valve. In examples, valve 602 may be disposed about a bottom portion of housing 300 and adjacent to internal cavity 310. Valve 602 may be coupled to external piping that leads to process vessel 200. Valve 602 may be actuated to release the particulate-containing fluid from internal cavity 310. As valve 602 is actuated, the external gas source may further pressurize diaphragm 302 to displace diaphragm into internal cavity 310. In examples, actuating valve 602 and pressurizing diaphragm 302 may occur simultaneously and/or at different stages of operation of dispensation unit 130. Diaphragm 302 may displace into internal cavity 310 up until diaphragm 302 is disposed along the walls of internal cavity 310, thus forcing out any remaining particulate-containing fluid through valve 602.

Figure 7:
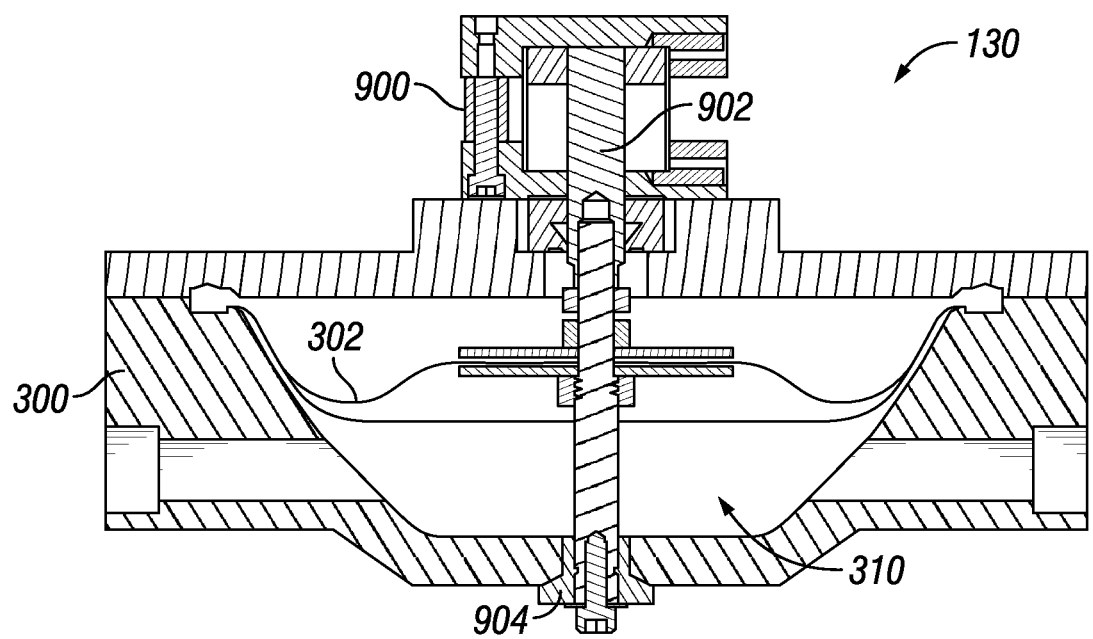
FIG. 7 illustrates another example of a dispensation unit with a convoluted diaphragm.
Figure 8:
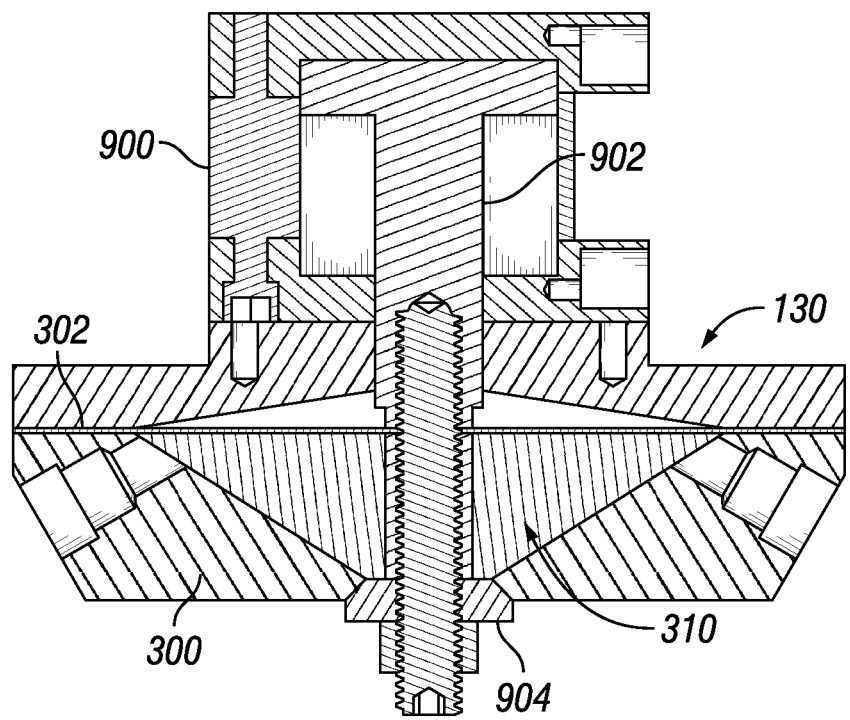
FIG. 8 illustrates an example of a dispensation unit with a pneumatic cylinder and a plunger.
Figure 9:
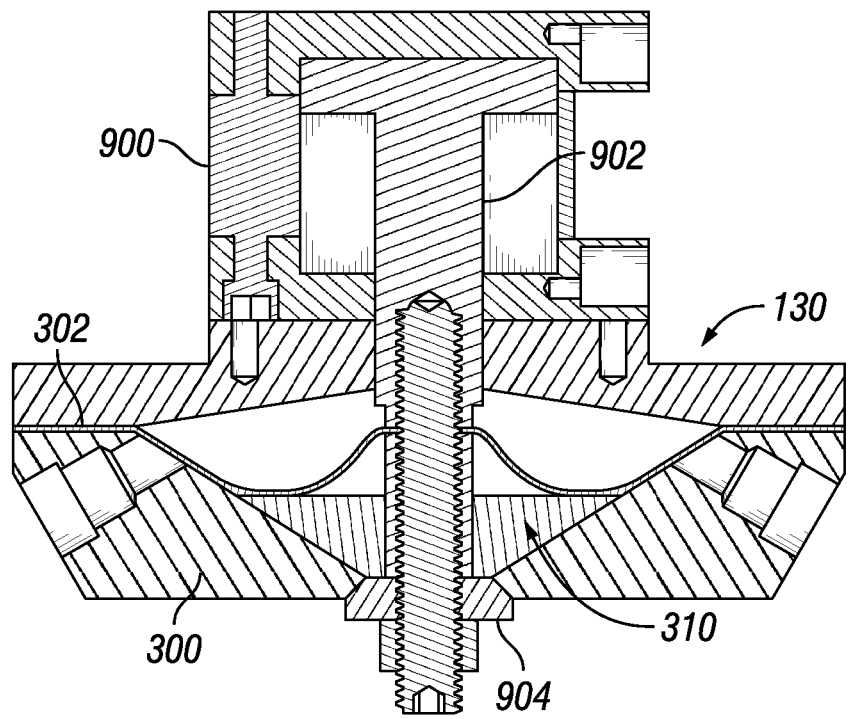
FIG. 9 illustrates an example of a dispensation unit with a pneumatic cylinder and a plunger.
Figure 10:
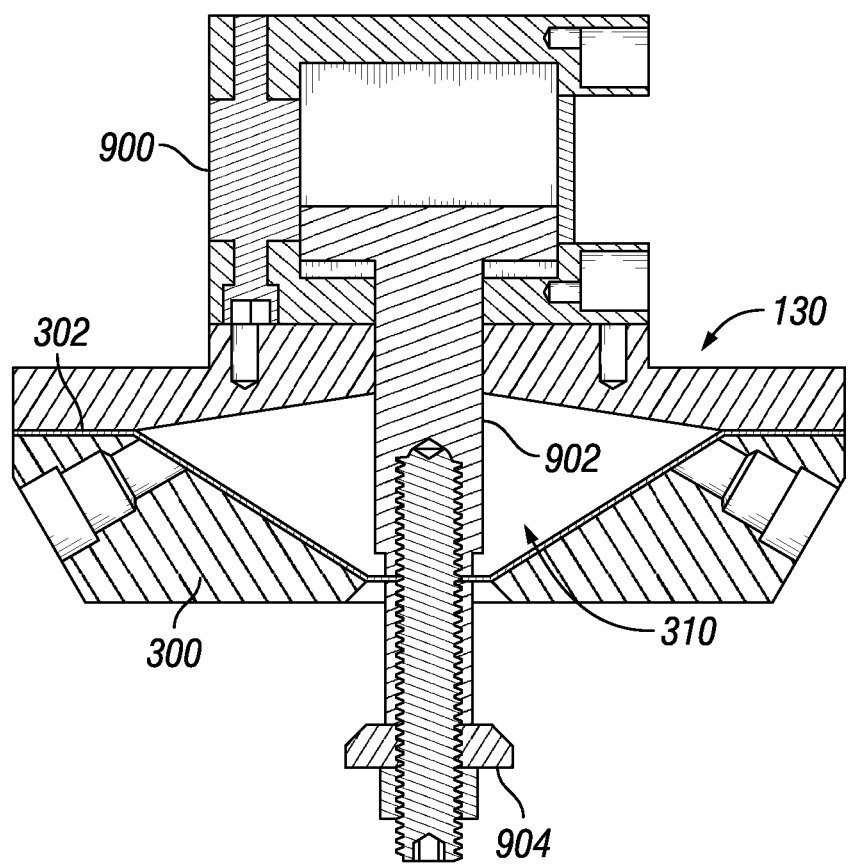
FIG. 10 illustrates an example of a dispensation unit with a pneumatic cylinder and a plunger.

FIGS. 7-10 illustrate examples of dispensation unit 130. As previously described, an external gas source may be used to pressurize diaphragm 302 to cause diaphragm 302 to displace. Without limitations, other suitable means may be employed to displace diaphragm 302. FIG. 7 illustrates an example of dispensation unit 130 using diaphragm 302 with a different shape and being actuated by a pneumatic cylinder 900. FIG. 8 illustrates an example of dispensation unit 130 with an initial position of pneumatic cylinder 900. FIG. 9 illustrates an example of dispensation unit 130 wherein diaphragm 302 is being pressurized while pneumatic cylinder 900 remains in an initial position. FIG. 10 illustrates an example of dispensation unit 130 with pneumatic cylinder 900 being actuated to further displace diaphragm 302. With reference to FIGS. 7-10, dispensation unit 130 may include pneumatic cylinder 900, a plunger 902, and a seal 904. In examples, pneumatic cylinder 900 may be actuated to displace plunger 902 thereby displacing diaphragm 302. As shown, diaphragm 302 may be clamped to plunger 902 and may be constructed in a convoluted shape within housing 300 (as best seen on FIG. 7). Seal 904 may be implemented rather than valve 602 (i.e., referring to FIG. 6) to prevent the particulate-containing fluid from exiting internal cavity 310. Without limitations, any suitable seal may be used as seal 904. Seal 904 may be disposed around plunger 902 and about a bottom portion of housing 300. As plunger 902, and subsequently diaphragm 302, actuate in a linear fashion, seal 904 may be removed from housing 300, therefore allowing the particulate-containing fluid to flow out of internal cavity 310. In example, the particulate-containing fluid may travel to process vessel 200 (i.e., referring to FIG. 2) for testing to determine properties of the particulate-containing fluid.

The preceding description provides various embodiments of systems and methods of use which may contain different method steps and alternative combinations of components. It should be understood that, although individual embodiments may be discussed herein, the present disclosure covers all combinations of the disclosed embodiments, including, without limitation, the different component combinations, method step combinations, and properties of the system.

Statement 1. A system for monitoring drilling fluid may comprise a fluid supply, wherein the fluid supply houses a drilling fluid; a pump, wherein the pump is fluidly connected to the fluid supply, and wherein the pump is configured to remove the drilling fluid from the fluid supply; a dispensation unit, wherein the dispensation unit is fluidly connected to the pump and the dispensation unit is configured to receive the drilling fluid and wherein the dispensation unit comprises: a housing, wherein the housing comprises: an internal cavity, wherein the internal cavity is an absence of material in the housing configured to be filled with a fluid; an inlet, wherein the inlet is a first opening in the housing fluidly coupling the housing to the fluid supply; and an outlet, wherein the outlet is a second opening in the housing fluidly coupling the housing to the fluid supply; and a top plate, wherein the top plate is configured to form a seal over the housing; and a diaphragm, wherein the diaphragm is disposed between the top plate and the housing; and a process vessel, wherein the process vessel is fluidly coupled to the dispensation unit and is configured to analyze and monitor the drilling fluid.

Statement 2. The system of statement 1, wherein the drilling fluid comprises sand, drill cuttings, clays, or combinations thereof.

Statement 3. The system of statement 1 or 2, wherein the process vessel comprises at least one sensor and wherein the at least one sensor is an electrical impedance sensor configured to be used in spectroscopy.

Statement 4. The system of statements 1-3, further comprising a coupling, wherein the coupling is attached to the top plate and wherein the coupling connects the dispensation unit to an external gas source and wherein the external gas source is configured to supply pressure onto the diaphragm through the coupling forming a fixed volume.

Statement 5. A dispensation unit may comprise a housing, wherein the housing may comprise an internal cavity, wherein the internal cavity is an absence of material in the housing configured to be filled with a fluid; an inlet, wherein the inlet is a first opening in the housing fluidly coupling the housing to a fluid supply; and an outlet, wherein the outlet is a second opening in the housing fluidly coupling the housing to the fluid supply; and a top plate, wherein the top plate is configured to form a seal over the housing; and a diaphragm, wherein the diaphragm is disposed between the top plate and the housing.

Statement 6. The dispensation unit of statement 5, further comprising a coupling, wherein the coupling is attached to the top plate and wherein the coupling connects the dispensation unit to an external gas source.

Statement 7. The dispensation unit of statements 5 or 6, wherein the top plate comprises at least one recess, wherein the at least one recess is disposed in an internal surface of the top plate.

Statement 8. The dispensation unit of statements 5-7, wherein the internal cavity is disposed concentric with the housing, wherein a height of the internal cavity is equivalent to a thickness of the housing, wherein a width of the internal cavity decreases as the thickness of the housing increases.

Statement 9. The dispensation unit of statements 5-8, wherein the internal cavity has a volume of about 20 milliliters to about 50 milliliters.

Statement 10. The dispensation unit of statements 5-9, wherein the housing further comprises a valve, wherein the valve is disposed at or near a bottom portion of the housing and adjacent to the internal cavity.

Statement 11. The dispensation unit of statement 10, further comprising a pneumatic cylinder, wherein the pneumatic cylinder is disposed on an outer surface of the top plate, a plunger, wherein the plunger is at least partially disposed in the pneumatic cylinder and traverses through the housing, and a seal, where the seal is disposed in place of the valve and wherein the plunger is at least partially disposed in the seal.

Statement 12. The dispensation unit of statements 5-9, wherein the diaphragm is coupled to the plunger, wherein the diaphragm displaces as the plunger displaces.

Statement 13. A method for analyzing a drilling fluid may comprise: pumping the drilling fluid through a dispensation unit, wherein the dispensation unit may comprise: a housing, wherein the housing comprises: an internal cavity, wherein the internal cavity is an absence of material in the housing configured to be filled with a fluid; an inlet, wherein the inlet is a first opening in the housing fluidly coupling the housing to a fluid supply; and an outlet, wherein the outlet is a second opening in the housing fluidly coupling the housing to the fluid supply; and a top plate, wherein the top plate is configured to form a seal over the housing; and a diaphragm, wherein the diaphragm is disposed between the top plate and the housing; and actuating the dispensation unit; and determining a property of the drilling fluid.

Statement 14. The method of statement 13, further comprising of applying a pressure to the diaphragm to displace the diaphragm into the internal cavity.

Statement 15. The method of statements 13 or 14, wherein the top plate comprises a coupling, wherein the coupling is connected to an external gas source, wherein the external gas source supplies a pressure to the diaphragm.

Statement 16. The method of statement 13, further comprising of displacing the diaphragm with a plunger.

Statement 17. The method of statement 16, wherein the dispensation unit further comprises a pneumatic cylinder and the plunger, wherein the diaphragm is coupled to the plunger, wherein the pneumatic cylinder is actuated to displace the plunger, wherein the diaphragm displaces as the plunger displaces.

Statement 18. The method of statement 13, wherein actuating the dispensation unit comprises of actuating a valve, wherein the valve is disposed at or near a bottom portion of the housing and adjacent to the internal cavity.

Statement 19. The method of statement 18, wherein pumping the drilling fluid comprises of filling the internal cavity with the drilling fluid.

Statement 20. The method of statement 19, wherein actuating the valve comprises of emptying the internal cavity of the particulate-containing fluid residing therein, wherein the drilling fluid is analyzed by a process vessel coupled to the dispensation unit.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A system for monitoring drilling fluid, comprising:
   a fluid supply, wherein the fluid supply houses a drilling fluid;
   a pump, wherein the pump is fluidly connected to the fluid supply, and wherein the pump is configured to remove the drilling fluid from the fluid supply;
   a dispensation unit, wherein the dispensation unit is fluidly connected to the pump and the dispensation unit is configured to receive the drilling fluid and wherein the dispensation unit comprises:
      a housing, wherein the housing comprises:
      an internal cavity, wherein the internal cavity is an absence of material in the housing configured to be filled with a fluid;
      an inlet, wherein the inlet is a first opening in the housing fluidly coupling the housing to the fluid supply; and
      an outlet, wherein the outlet is a second opening in the housing fluidly coupling the housing to the fluid supply; and
      a top plate, wherein the top plate is configured to form a seal over the housing; and
      a diaphragm, wherein the diaphragm is disposed between the top plate and the housing; and
   a process vessel, wherein the process vessel is fluidly coupled to the dispensation unit and is configured to analyze and monitor the drilling fluid.

2. The system of claim 1, wherein the drilling fluid comprises sand, drill cuttings, clays, or combinations thereof.

3. The system of claim 1, wherein the process vessel comprises at least one sensor and wherein the at least one sensor is an electrical impedance sensor configured to be used in spectroscopy.

4. The system of claim 1, further comprising a coupling, wherein the coupling is attached to the top plate and wherein the coupling connects the dispensation unit to an external gas source and wherein the external gas source is configured to supply pressure onto the diaphragm through the coupling forming a fixed volume.

5. A dispensation unit, comprising:
a housing, wherein the housing comprises:
an internal cavity, wherein the internal cavity is an absence of material in the housing configured to be filled with a fluid;
an inlet, wherein the inlet is a first opening in the housing fluidly coupling the housing to a fluid supply; and
an outlet, wherein the outlet is a second opening in the housing fluidly coupling the housing to the fluid supply; and
a top plate, wherein the top plate is configured to form a seal over the housing; and
a diaphragm, wherein the diaphragm is disposed between the top plate and the housing.

6. The dispensation unit of claim 5, further comprising a coupling, wherein the coupling is attached to the top plate and wherein the coupling connects the dispensation unit to an external gas source.

7. The dispensation unit of claim 5, wherein the top plate comprises at least one recess, wherein the at least one recess is disposed in an internal surface of the top plate.

8. The dispensation unit of claim 5, wherein the internal cavity is disposed concentric with the housing, wherein a height of the internal cavity is equivalent to a thickness of the housing, wherein a width of the internal cavity decreases as the thickness of the housing increases.

9. The dispensation unit of claim 5, wherein the internal cavity has a volume of 20 milliliters to 50 milliliters.

10. The dispensation unit of claim 5, wherein the housing further comprises a valve, wherein the valve is disposed at or near a bottom portion of the housing and adjacent to the internal cavity.

11. The dispensation unit of claim 10, further comprising a pneumatic cylinder, wherein the pneumatic cylinder is disposed on an outer surface of the top plate, a plunger, wherein the plunger is at least partially disposed in the pneumatic cylinder and traverses through the housing, and a seal, where the seal is disposed in place of the valve and wherein the plunger is at least partially disposed in the seal.

12. The dispensation unit of claim 11, wherein the diaphragm is coupled to the plunger, wherein the diaphragm displaces as the plunger displaces.

13. A method for analyzing a drilling fluid, comprising:
pumping the drilling fluid through a dispensation unit, wherein the dispensation unit comprises:
a housing, wherein the housing comprises:
an internal cavity, wherein the internal cavity is an absence of material in the housing configured to be filled with a fluid;
an inlet, wherein the inlet is a first opening in the housing fluidly coupling the housing to a fluid supply; and
an outlet, wherein the outlet is a second opening in the housing fluidly coupling the housing to the fluid supply; and
a top plate, wherein the top plate is configured to form a seal over the housing; and
a diaphragm, wherein the diaphragm is disposed between the top plate and the housing; and
actuating the dispensation unit; and
determining a property of the drilling fluid.

14. The method of claim 13, further comprising of applying a pressure to the diaphragm to displace the diaphragm into the internal cavity.

15. The method of claim 14, wherein the top plate comprises a coupling, wherein the coupling is connected to an external gas source, wherein the external gas source supplies a pressure to the diaphragm.

16. The method of claim 13, further comprising of displacing the diaphragm with a plunger.

17. The method of claim 16, wherein the dispensation unit further comprises a pneumatic cylinder and the plunger, wherein the diaphragm is coupled to the plunger, wherein the pneumatic cylinder is actuated to displace the plunger, wherein the diaphragm displaces as the plunger displaces.

18. The method of claim 13, wherein actuating the dispensation unit comprises of actuating a valve, wherein the valve is disposed at or near a bottom portion of the housing and adjacent to the internal cavity.

19. The method of claim 18, wherein pumping the drilling fluid comprises of filling the internal cavity with the drilling fluid.

20. The method of claim 19, wherein actuating the valve comprises of emptying the internal cavity of the particulate-containing fluid residing therein, wherein the drilling fluid is analyzed by a process vessel coupled to the dispensation unit.

* * * * *